United States Patent

Hynson et al.

[11] Patent Number: 6,162,181
[45] Date of Patent: Dec. 19, 2000

[54] BLOOD PRESSURE MEASUREMENT FROM THE HAND

[76] Inventors: James M. Hynson, 1674 32nd Ave., San Francisco, Calif. 94122; Jeffrey A. Katz, 1440 Madera Way, Millbrae, Calif. 94030

[21] Appl. No.: 09/373,424

[22] Filed: Aug. 16, 1999

[51] Int. Cl.[7] .................................................. A61B 5/00
[52] U.S. Cl. ...................... 600/485; 600/490; 600/499; 600/500
[58] Field of Search .................................. 600/485, 490, 600/493–6, 499, 500

[56] References Cited

U.S. PATENT DOCUMENTS

| 4,033,337 | 7/1977 | Raczkowski | 600/494 |
| 5,577,508 | 11/1996 | Medero | 600/494 |
| 5,727,559 | 3/1998 | Hynsone et al. | 600/485 |

*Primary Examiner*—Robert L. Nasser
*Attorney, Agent, or Firm*—William W. Jones

[57] ABSTRACT

A method and assembly oscillometrically measures systolic, mean and diastolic blood pressures by inflating a form fitting cuff disposed over the Palmar Arch of the hand, and subsequently deflating the cuff stepwise, The arterial blood supply to the hand, which is very rich, lies relatively close to the surface of the palm. Cuff pressure oscillations can be sensed with an inflatable glove or mitten type cuff. A full or partial glove, mitten, or the like, with openings for reception of portions of the fingers and thumb can be used. Inflation of the cuff allows the assembly to be used to measure arterial blood pressure on either hand of a patient.

8 Claims, 3 Drawing Sheets

BLOOD PRESSURE MEASUREMENT FROM THE HAND

FIELD OF THE INVENTION

This invention relates to blood pressure ("BP") measurement and more particularly to a method and apparatus to measure BP by utilizing the hand.

BACKGROUND ART

The measurement of systolic, diastolic, and mean blood pressure values by measuring cuff pressure oscillations caused by patient blood vessel pulses during deflation of the cuff is a known technique. Oscillometric blood pressure measurement is taken at numerous anatomical sites in the body including the upper arm, forearm, wrist, finger, ankle, calf and thigh. These sites are roughly cylindrical in shape and easily lend themselves to placement of a wrap-around rectangular inflatable cuff to intermittently restrict blood flow.

At cuff pressures above systolic pressure, minimal blood flow occurs and no pressure oscillations are received in a monitoring device. As cuff pressure is decreased, blood vessel oscillations are sensed in the monitoring device and the amplitude of these oscillations becomes larger. The cuff pressure at which oscillations are largest is typically considered to correlate with mean pressure. As pressure in the cuff is decreased further, oscillations become smaller and eventually are no longer present. Mean, systolic and diastolic pressures are sensed and determined by computer analysis in the monitoring device of the changes in the oscillation amplitudes during cuff deflation as is known in the art.

Traditional methods of oscillometrically measuring BP on the arm with a rectangular pressure cuff has several disadvantages. Firstly, the upper arm, the most commonly used site, is difficult to use if the patient is obese, or if the arm is conically shaped. Secondly, the use of the upper arm and other sites that include a substantial amount of soft issue, particularly fat and muscle, tend to be associated with more patient discomfort. Thirdly, measurement of BP in the arm or forearm is contra-indicated in some patients, such as those who have undergone mastectomy surgery with lymph node dissections, and patients with renal dialysis grafts in their arms. Though this restriction is typically limited to only one arm, these patients often have other devices and intravenous catheters placed on the opposite arm, and the measurement of BP via the arm typically interferes with the function of these devices. Finally, the upper arm is prone to artifacts during surgical procedures because patients arms are often tucked in at their sides during surgery. If a surgeon should happen to lean against a patient while operating on the upper abdomen or chest, the BP monitor may have difficulty separating BP oscillations from random oscillations generated by external pressure applied to the cuff by the surgeon. Traditional rectangular arm cuffs are difficult to use by an individual without assistance, because two hands are typically required to attach and use the cuff. Finger BP measurements are prone to error because of peripheral vasoconstriction, which is a common occurrence in the digits.

It would be desirable to provide a practical and readily usable method and apparatus to measure blood pressure which does not employ the traditional rectangular blood pressure cuff.

DISCLOSURE OF THE INVENTION

It is an object of this invention to provide a blood pressure cuff that is easy to use by an individual and others.

It is a further object of this invention to provide a method and an apparatus that can be used to measure the blood pressure of the obese.

it is an additional object of this invention to provide a method and apparatus of the character described which is operable to minimize patient discomfort during measurement of patient blood pressure.

It is another object of the invention to provide a method and apparatus of the character described which is operable to produce accurate blood pressure determinations during patient surgery.

It is yet another object of this invention to provide a method and apparatus of the character described which utilizes a body site that is more proximal to the heart than the fingers.

It is a still further object of this invention to provide a method and apparatus of the character described which utilizes a practical location for determining blood pressure if the patient has had lymph node dissections; has renal dialysis grafts; or has arm shunts, IV's or other arm-mounted devices.

This invention relates to a method and apparatus for measuring blood pressure by utilizing a form fitting cuff which is disposed in proximity to one or more of the major arteries in the palm of the hand. The palm of the hand has not been a site for BP measurement because it lacks the cylindrical characteristics of typical anatomic sites for blood pressure measurement. Nevertheless, the arterial blood supply to the palm of the hand, which is very rich, lies relatively close to its surface. The normal blood supply to the palm of the hand is comprised of the ulnar and radial arteries that converge to form the Palmar Arch. The Palmar Arch then supplies blood to the deep tissues of the hand, as well as to the digital arteries which supply blood flow to the fingers. BP oscillations can be sensed from an inflatable glove or mitten type cuff. A partial glove or mitten, or the like, i.,e., with portions of the fingers and thumb exposed, can also achieve this function by intermittently restricting blood flow using a varying pressure in the glove/mitten.

The method and apparatus of this invention achieves the aforesaid objects as follows. Use of the upper arm or other sites which may include a substantial amount of soft issue, e.g., fat and muscle, is avoided thereby minimizing patent discomfort. Since the hand is largely bone, tendon, and ligament, patient discomfort is minimized. Since the hand has no lymphatic channels, measurement of BP from the hand can usually be performed in an limb which has undergone lymph node dissection. Similarly, the hand is usually distal to dialysis grafts and is often distal to other venous access devices. Therefor, measurement of BP from the hand will not interfere with the function of more proximal vascular access devices.

Compared with measurement of BP via the wrist, hand BP monitoring can result in stronger oscillations because of the larger exposure of the underlaying arteries to the pressure mitt. Hand BP monitoring is easier for a lone individual to employ because the hand to which the cuff is fitted can participate in the cuff placement, an advantage when compared with upper arm measurement with a standard rectangular cuff. Stated another way, it's as easy as putting on a glove. The hand also provides an accessible site which eliminates the surgical artifact problem.

Furthermore, when compared with finger BP monitoring, Palmar Arch BP measurement provides a more proximal site of measurement, thus minimizing the finger vasoconstriction problem. When employing the method and apparatus of this invention, the hand should be maintained close to the level of the heart for accurate measurement. This is true for any site; however, in the case of the upper arm, the BP cuff is always close to the correct position relative to the heart. Thus, hand BP monitoring should be performed with the hand positioned at the level of the heart. When lying supine, this can be achieved by maintaining the hands at the patient's side. When standing or sitting, this can be easily achieved by placing the hand over the heart.

These and other objects, features and advantages of the invention will become more readily apparent from the following detailed description of the invention when taken in conjunction with the accompanying drawings, in which:

DETAILED DESCRIPTION OF THE INVENTION

Figure 1:
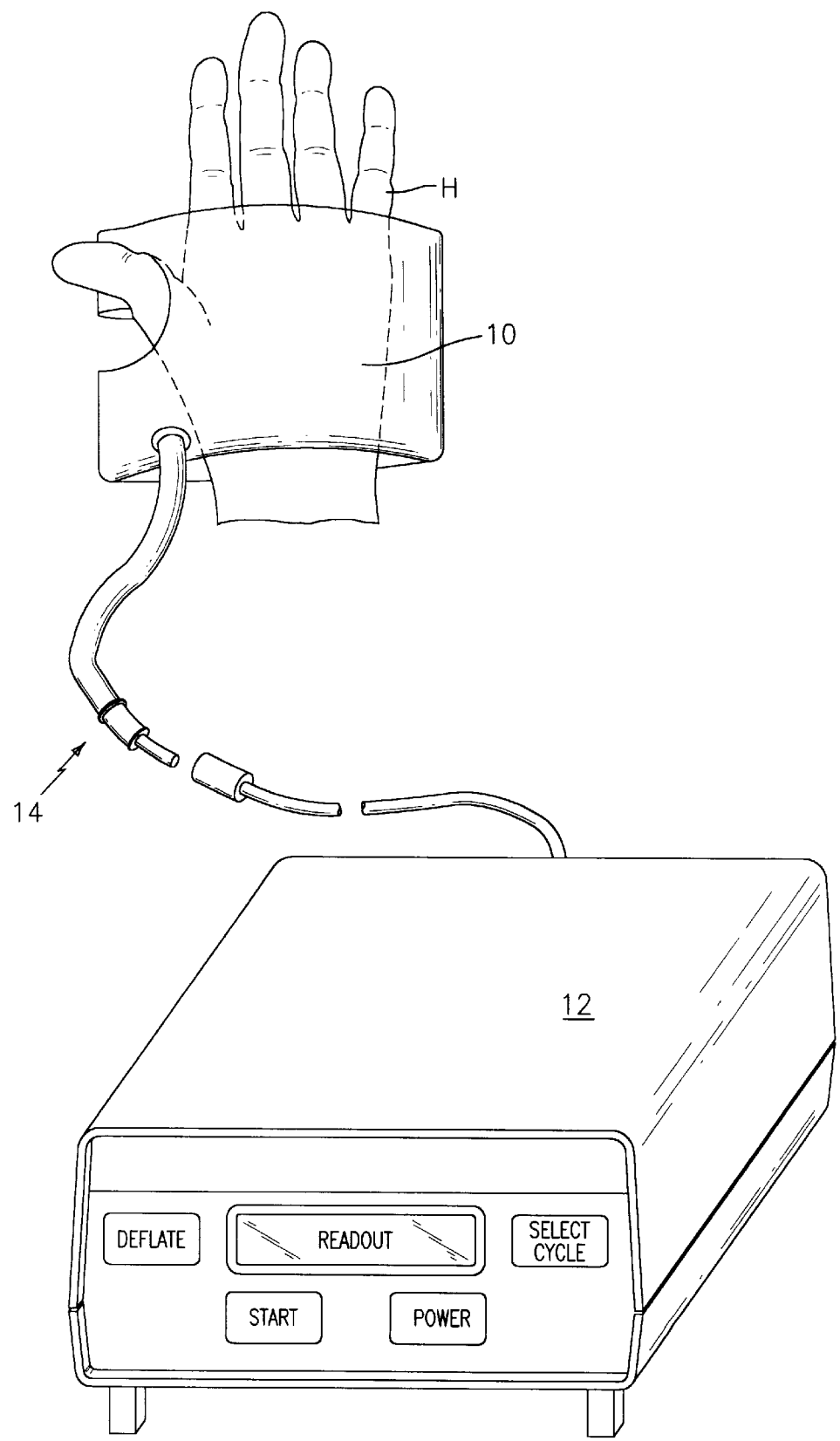
FIG. 1 is a perspective view of an embodiment of a cuff and monitoring assembly used in accordance with this invention.

Referring now to the drawings, in FIG. 1 there is shown a glove-shaped pressure cuff 10 for affixation to a patient's hand H; a cuff-inflation and analysis device 12; and a pneumatic coupling 14 connecting the inflation device 12 and the cuff 10.

Figure 2:
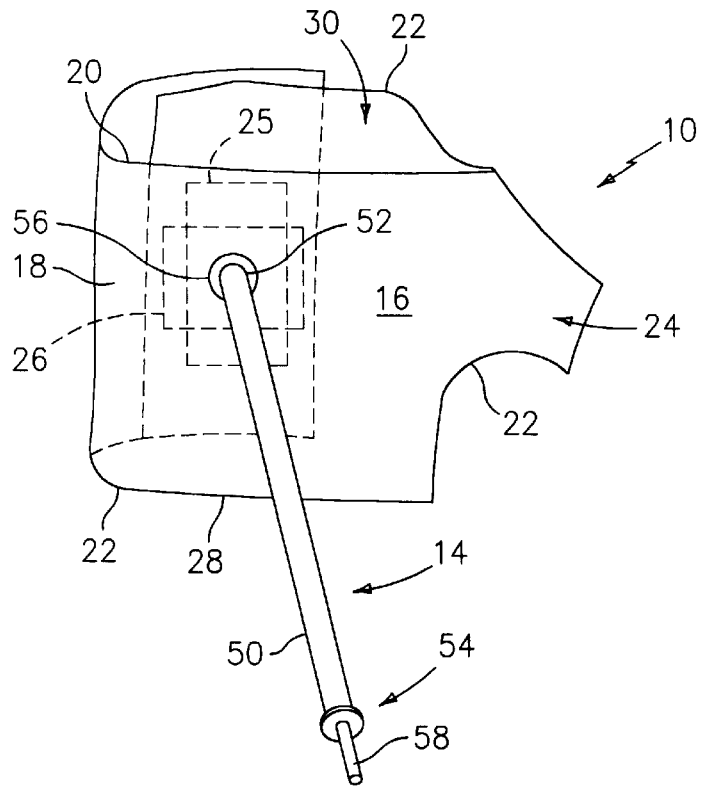
FIG. 2 is a plan view of a first embodiment of a cuff used with the assembly of FIG. 1.

In the embodiment of the pressure cuff 10 which is shown in FIG. 2, the cuff has a glove-shaped body 16 without fingers, and having an outer surface 18 and an inner surface 20 which contacts the hand H. The edges 22 of the outer and inner surfaces of the cuff 10 are bonded together to allow the cuff 10 to receive and maintain pneumatic pressure with minimal pressure leakage. Pneumatic pressure is introduced between the surfaces 18 and 20 by the device 12 and causes the inner surface 20 of the cuff 10 to be forced inwardly against the hand H so as to minimize blood flow through the palm of the hand H.

The glove-shaped body 16 has an opening 24 through which the patent's thumb can protrude. The inner surface 20 of the cuff 10 has a first half 25 with a hook and loop closure (or the like, e.g., laces, belt and buckle, or snaps, etc.) which is affixed on an end thereof distal from the thumb opening 24. The outer surface 18 of the cuff 10 has a second half 26 of the closure affixed thereto in a position to adjustably co-operate with the first half 25 of the closure to allow the body 16 to be snugly fitted upon the patient's hand H.

Before determining a patient's blood pressure, the closure components 24 and 26 are separated, thereby allowing the patient to slip his or her thumb through the thumb opening 22. The patient can easily grip the body 16 with the hand from which blood pressure is to be determined while closing the closures around the back of the hand H on the inner and outer sides of the cuff 10. If the cuff 10 is properly attached to the hand H, the fingers extend through the finger opening 28, the thumb projects through the thumb opening 24, and the wrist extends through the wrist opening 30.

Figure 3:
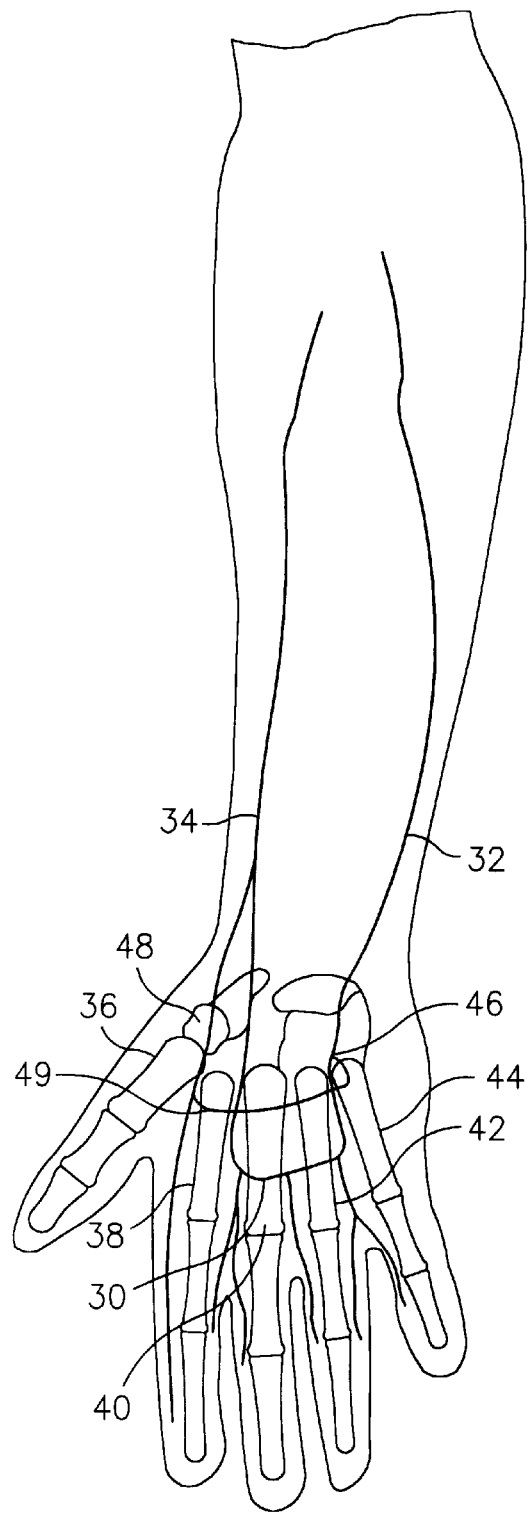
FIG. 3 is an schematic view of the arterial anatomy of the portion of the hand to which the assembly of FIG. 1 is applied.

Referring to FIG. 3, ideally, the body 16 is disposed in close, non-invasive contact with the Palmar Arch 30, which is a confluence of the ulnar and radial arteries 32 and 34, respectively. As is well known, the hand H has five metacarpals 36, 38, 40, 42 and 44 respectively, the hamate 46 arid trapezium 48. The ulnar artery 32 passes in close proximity to the hook of the hamate bone 46 and then divides into the deep 49 and superficial Palmar branches. Similarly, the radial artery 34 passes through the wrist between the second 38 and third 40 metacarpals and usually, but not always, joins the ulnar artery to form the Palmar Arch 30. Because of the location of the Palmar Arch, it is important to place the body of the cuff 10 in overlying proximity therewith. Therefore, the cuff 10 should be placed in close proximity to, and around the second and fifth metacarpals to properly place the cuff. Ideally the cuff body extends in close proximity to, and around a distal side of the first metacarpal 36 near the thumb 48. If the patient is missing metacarpals, the cuff 10 can be placed along those metacarpals that are remaining. Because of the anatomy of the Palmar Arch, which may be incomplete, the radial artery, including where the radial artery passes near the thumb and/or ulnar arteries, can provide the pressure pulses necessary for proper blood pressure measurement.

Referring to FIG. 2, the pneumatic coupling 14 includes a tube 50 having a first end 52 and a second end 54; a nipple 56 sealingly attached to the outer layer of the cuff 10 for infusing pneumatic pressure into the cuff 10, and sealingly extending into the first end 52 of the tube 50; a portion of a standard pneumatic coupling 58 sealingly attached to the second end 54 of the tube 50 for coupling with the computer controlled pump 12.

As is known in the art, the device 12 automatically inflates the cuff 10 to an initial pressure calculated to be above the subject's systolic blood pressure. Such a device 12 is manufactured by CAS Medical Systems, Inc., Branford, Conn. Operation of the device 12, as well as components of the device, such as pressure transducers, and pump and the like (not shown), are controlled by an onboard computer (not shown). The device 12 automatically lowers the pressure in the cuff 10 stepwise, preferably in increments of 10% of previous pressure, and cuff pressure oscillations created by the patient's blood flow are detected and stored as a dependent variable at each cuff pressure step during the deflating procedure. The cuff pressures at each step are also noted and stored as the independent variable by the device 12. If the device 12 has detected that mean pressure is passed by reason of declining oscillations, the device 12 identifies the maximum oscillation detected and program a deflating mechanism (not shown) to continue to deflate the cuff 10 to a pressure that produces oscillations of about 0.6 of the maximum oscillation measured. This ensures that the cuff 10 is deflated past the diastolic pressure value. Once this level is reached, the device 12 empties the cuff 10 of air. The device 12 then reviews the stored oscillations, identifies the maximum oscillation value, and its cuff pressure, and identifies an oscillation value that occurred before maximum, and another oscillation value that occurred after maximum, as well as their respective cuff pressure values. Once the three oscillation values are determined, the computer fits the three oscillation values to a parabolic curve and calculates the peak oscillation value for that particular curve which has been fitted to the measured oscillations. The computer then uses the calculated parabolic equation to determine the cuff pressure at which this calculated peak oscillation would have occurred, this cuff pressure being the mean blood pressure value. This pressure is stored as the "true" mean blood pressure.

In order to determine the "true" systolic pressure, the computer identifies the oscillation that is 0.75 of the calculated maximum oscillation, and then reviews the stored oscillations that occurred prior to the maximum measured oscillation. The computer identifies the two prior oscillations that straddle the calculated 0.75 maximum oscillation and notes the measured cuff pressures associated with each of the straddling oscillations. The compiler then identifies the slope of the line connecting the two straddling oscillations and notes where, along that slope, the calculated 0.75 oscillation lies. Using the location of this point along the slope, the computer interpolates to determine what cuff pressure conforms to that point along the slope. The same procedure is followed to calculate "true" diastolic pressure using the 0.8 factor with the calculated maximum oscillation.

The computer controlled pump also measures pulse rate by measuring and storing the duration of each pause between the beginnings of successive oscillation rises. The beginning and ending data points are discarded and the measured actual pause durations are averaged. The actual pauses are then compared to the average, and any individual values which vary from the average by more than 10% are discarded. The remaining data is then re-averaged to calculate the accepted pulse rate. The pulse rate, systolic, diastolic, and mean pressures are all displayed, preferably on a digital readout.

For accurate measurement, the hand needs to be held at the level of the heart. When lying supine, this can be achieved by maintaining the hands at the patient's side. When standing or sitting, this can be easily achieved by holding the hand over the heart.

Figure 4:
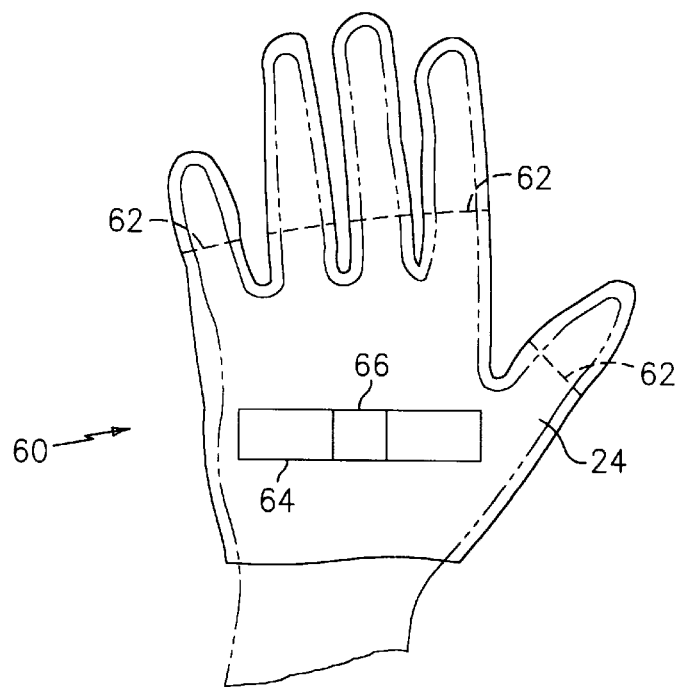
FIG. 4 is a plan view of a second embodiment of a cuff used with the embodiment of FIG. 1.

Referring to FIG. 4, it is seen that the cuff 10 may take the form of a glove 60, either with complete fingers, or like a bicycle glove with glove material traveling partially along each finger (e.g. remove material above the broken line 62). Ideally, the finger portions of the complete glove would have the same inner and outer sides extended along the length of the fingers to apply pressure uniformly along the fingers thereby minimizing discomfort caused by finger bloating during the application of higher cuff pressures during monitoring. The glove has a thumb opening 24 for proper orientation of the cuff 10 about the palm and encircles the hand H. The glove may have a strap 64 having a hook and loop (or the like) closure 66 to enable the glove to be snugly fitted to the hand.

One of ordinary skill in the art will recognize from the teachings herein that the shape of the cuff 10 is dependent on its ability to properly occlude the blood vessels in the Palmar Arch area of the palm and to receive cuff pressure oscillations emanating from the Palmar Arch during measurement of blood pressure. As such, placement of the cuff around the metacarpals of the second and fifth fingers, is important. Utilizing a thumb receptor such as the opening 22 in the cuff 10 as a mechanism to properly place the cuff about these metacarpals as locators over the Palmar Arch is therefore ideal. Placement of a cuff around the thumb itself will cause the thumb to rotate towards the little finger minimizing the ability of the device 12 to property receive pressure oscillations from the hand during blood pressure measurement. One of ordinary skill in the art then will also recognize from the teachings herein that the cuff may have a mitten (or other) shape as long as the thumb is prevented from rotating towards the palm during blood pressure measurement. A separate opening for the thumb in a mitten (or other shape) accomplishes this goal. One of ordinary skill in the art will also recognize that the cuff may be slightly oversized to ensure that any variations in the anatomy of the vessels in each patent's hand do not act to impede proper blood pressure measurement. It is noted that the glove or mitten will have both the palm side, and the opposite side, inflatable, thus making the device usable on either of the patient's hands.

One of ordinary skill in the art will also recognize from the teachings herein that the device is applicable for use with distal appendages of the body depending from limbs. For instance, the Dorsalis Pedis artery and the Domal Arch provide, similarly to the Palmar Arch, will create arterial pulsations from which blood pressure may be measured. A cuff 10 similar to the one described above may include an opening similar to the opening 30 described above for one's ankle; an opening similar to the opening 24 described above for one's heel; and an opening similar to the opening 28 described above for one's toes.

Since many changes and variations of the disclosed embodiments of the invention may be made without departing from the inventive concept, it is not intended to limit the invention otherwise than as required by the appended claims.

What is claimed is:

1. A method for obtaining blood pressure measurements from an arterial blood vessel in the palm of an individual's hand, said method comprising:

a) the step of positioning a pressure cuff over said arterial blood vessel in the individual's palm so that blood flow in said arterial blood vessel may be controlled by inflation of said cuff;

b) the step of inflating the pressure cuff to a pressure which will occlude blood flow in said arterial blood vessel;

c) the steps of lowering the pressure in said cuff by deflating said cuff in step wise increments; and d) the steps of determining the patient's blood pressure from cuff pressure oscillations which are sensed from said cuff at each of said cuff pressure deflation increments.

2. The method of claim 1 wherein said cuff comprises a body portion for covering the palm and the back of the hand, and has an opening through which the individual's thumb protrudes.

3. A method for obtaining blood pressure measurements from the Palmar Arch in a patient's hand, said method comprising the steps of:

a) positioning an inflatable pressure cuff about the patient's hand in overlying relationship with the Palmar Arch so that said blood flow in the Palmar Arch may be electively controlled by application of fluid pressure in said cuff;

b) inflating said cuff to a pressure which occludes blood flow through the Palmar Arch; and c) deflating said cuff stepwise to a pressure which allows unimpeded blood flow through the Palmar Arch, while oscillometrically measuring the patient's blood pressure from cuff pressure oscillations at each cuff deflation step, so as to determine the patient's systolic, mean, and diastolic arterial blood pressures.

4. A method for obtaining blood pressure measurements from an artery located in the palm of a patient's hand, said method comprising the steps of:

a) applying a form-fitting pressure cuff to the patient's palm so as to position said cuff in overlying relationship with said palm artery;

b) inflating said cuff to an initial cuff pressure which occludes blood flow through said palm artery;

c) deflating said cuff stepwise from said initial cuff pressure to a final cuff pressure which allows unrestricted blood flow through said palm artery; and d) measuring pressure oscillations in said cuff during said stepwise deflation of said cuff so as to determine systolic, mean, and diastolic arterial blood pressures.

5. An assembly for obtaining oscillometric blood pressure measurements from an arterial blood vessel contained in the palm of a patient's hand, said assembly comprising:

a) a pressure cuff having a body portion for extending around the palm and the back of the hand and having an opening through which the patient's thumb can protrude;

b) a device for inflating said cuff above systolic blood pressure and for subsequently incrementally deflating said cuff stepwise to a pressure which is below diastolic blood pressure; and c) means for sensing stepwise pressure oscillations in said cuff as said cuff is deflated so as to determine systolic, mean and diastolic blood pressures from said arterial blood vessel.

6. The assembly of claim 5 wherein portions of said pressure cuff covering both the back and palm of the patient's hand are inflatable so as to enable use of the pressure cuff on either hand of the patient.

7. An assembly for obtaining oscillometric blood pressure measurements from an arterial blood vessel contained in a patient's distal appendage, said assembly comprising:

a) an inflatable pressure cuff having a body portion with a first side for extending around a side of the appendage proximal to the arterial blood vessel, and having a second side for extending around an opposite side of the appendage, said pressure cuff having at least one opening through which patient digits can protrude;

b) a device for inflating said cuff above systolic blood pressure and for subsequently incrementally deflating said cuff stepwise to a pressure which is below diastolic blood pressure; and c) means for sensing stepwise pressure oscillations in said cuff as said cuff is deflated so as to determine systolic, mean and diastolic blood pressures from said arterial blood vessel.

8. The assembly of claim 7 wherein both of said first and second sides of said body portion are inflatable.

* * * * *